United States Patent
Miyamoto et al.

(10) Patent No.: US 6,916,641 B2
(45) Date of Patent: Jul. 12, 2005

(54) (R)-2-HYDROXY-3-PHENYLPROPIONATE (D-PHENYLLACTATE) DEHYDROGENASE AND GENE ENCODING THE SAME

(75) Inventors: Koichi Miyamoto, Odawara (JP); Naomi Sumida, Odawara (JP); Naoki Midoh, Odawara (JP); Takeshi Murakami, Odawara (JP); Rainer Zocher, Berlin (JP); Horst Kleinkauf, Berlin (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 10/258,472

(22) PCT Filed: Apr. 26, 2001

(86) PCT No.: PCT/JP01/03645
§ 371 (c)(1),
(2), (4) Date: Nov. 7, 2002

(87) PCT Pub. No.: WO01/81563
PCT Pub. Date: Nov. 1, 2001

(65) Prior Publication Data
US 2003/0186410 A1 Oct. 2, 2003

(30) Foreign Application Priority Data
Apr. 26, 2000 (JP) ..................................... 2000-125449

(51) Int. Cl.$^7$ ............................ C12N 9/04; C12N 1/20; C12N 15/00; C12P 21/04; C07H 21/04

(52) U.S. Cl. ............................. 435/190; 435/4; 435/6; 435/69.1; 435/71.1; 435/252.3; 435/320.1; 435/26; 536/23.2

(58) Field of Search ............................. 435/190, 252.3, 435/320.1, 69.1, 71.1, 4, 6, 26, 440; 536/23.2

(56) References Cited

FOREIGN PATENT DOCUMENTS

| WO | 97/20945 | 6/1997 |
| WO | 01/18179 | 3/2001 |
| WO | 01/18219 | 3/2001 |

OTHER PUBLICATIONS

Chistoserdova et al. NCBI—Accession Q59516, 1997.*
Wilks et al. Biochemistry. Sep. 1, 1992;31(34):7802–6.*
Hayao Taguchi et al., "D–Lactate Dehydrogenase Is a Member of the D–Isomer–specific 2–Hydroxyacid Dehydrogenase Family", The Journal of Biological Chemistry, vol. 266, No. 19, pp. 12588–12594, Jul. 5, 1991.
Wolfram Weckwerth et al., "Biosynthesis of PF1022A and Related Cyclooctadepsipeptides", The Journal of Biological Chemistry, vol. 275, No. 23, pp. 17909–17915, Jun. 9, 2000.

* cited by examiner

Primary Examiner—Manjunath Rao
Assistant Examiner—Yong Pak
(74) Attorney, Agent, or Firm—Wenderoth, Lind & Ponack L.L.P.

(57) ABSTRACT

An objective of the present invention is to provide a D-phenyllactic acid dehydrogenase. Another objective of the present invention is to provide a gene which encodes the D-phenyllactic acid dehydrogenase. A D-phenyllactic acid dehydrogenase according to the present invention is a protein comprising an amino acid sequence of the amino acid sequence of SEQ ID NO: 2 or a modified amino acid sequence of the amino acid sequence of SEQ ID NO: 2 that has one or more modifications selected from a substitution, a deletion, an addition and an insertion and has D-phenyllactic acid dehydrogenase activity. A D-phenyllactic acid dehydrogenase gene according to the present invention comprises a nucleotide sequence which encodes the D-phenyllactic acid dehydrogenase, for example the nucleotide sequence of SEQ ID NO: 1.

12 Claims, 1 Drawing Sheet

SEQUENCE LISTING

<160> NUMBER OF SEQ ID NOS: 12

<210> SEQ ID NO 1
<211> LENGTH: 1011
<212> TYPE: DNA

```
<213> ORGANISM: Mycelia sterilia
<220> FEATURE:
<221> NAME/KEY: CDS
<222> LOCATION: (1)..(1008)

<400> SEQUENCE: 1 atg gcc caa gca caa cca cag acc cat tgg gtt att gtc gca ttg gag        48
Met Ala Gln Ala Gln Pro Gln Thr His Trp Val Ile Val Ala Leu Glu
 1               5                  10                  15 act ttc ttc tgt ccg ctc ccc gat ttc act ctc ccg gcg ccg cat acc        96
Thr Phe Phe Cys Pro Leu Pro Asp Phe Thr Leu Pro Ala Pro His Thr
             20                  25                  30 tgc gag ttc cgg aac tat gat cgg acg agg cca gac caa ata gcc gag       144
Cys Glu Phe Arg Asn Tyr Asp Arg Thr Arg Pro Asp Gln Ile Ala Glu
         35                  40                  45 cga att cgt gat gcc gac atc gtg atc atg aca atc ttg ccg atg ccg       192
Arg Ile Arg Asp Ala Asp Ile Val Ile Met Thr Ile Leu Pro Met Pro
     50                  55                  60 gcg gat gtt ctg agc gcg gag gca agc ccg cgc cta aag atg tta tct       240
Ala Asp Val Leu Ser Ala Glu Ala Ser Pro Arg Leu Lys Met Leu Ser
 65                  70                  75                  80 atc att gct tca ggc acg gac acc gta gac ttg gcg acg tgc cgg gct       288
Ile Ile Ala Ser Gly Thr Asp Thr Val Asp Leu Ala Thr Cys Arg Ala
                 85                  90                  95 cgg ggg ata gtc gta gcc aac acg ccg cat tgc aat gtc acc acg gtc       336
Arg Gly Ile Val Val Ala Asn Thr Pro His Cys Asn Val Thr Thr Val
            100                 105                 110 acc gag cac gta ttc gcg ctc tat ttt gcg aca cgc cgc tcc ata gtg       384
Thr Glu His Val Phe Ala Leu Tyr Phe Ala Thr Arg Arg Ser Ile Val
        115                 120                 125 gca aca cat ctg ctc acg cgc gcc ggc gac tgg gtc acc aag gga tcc       432
Ala Thr His Leu Leu Thr Arg Ala Gly Asp Trp Val Thr Lys Gly Ser
    130                 135                 140 cag cag agc acg atg aac ggg ccc gac ggg aaa ccg ccg atg aca tgt       480
Gln Gln Ser Thr Met Asn Gly Pro Asp Gly Lys Pro Pro Met Thr Cys
145                 150                 155                 160 cgc gac gag ctc gtc ggc atc atc ggc tac ggc gca ata ggg aag aac       528
Arg Asp Glu Leu Val Gly Ile Ile Gly Tyr Gly Ala Ile Gly Lys Asn
                165                 170                 175 gtc gag aca atg gcc aga tca tta ggc atg aaa acc gtc atc gcc ggg       576
Val Glu Thr Met Ala Arg Ser Leu Gly Met Lys Thr Val Ile Ala Gly
            180                 185                 190 cac aag ggg gct gcc tcg acg cca gag ggc cgc gcc cca ttc gag acc       624
His Lys Gly Ala Ala Ser Thr Pro Glu Gly Arg Ala Pro Phe Glu Thr
        195                 200                 205 gtc atc cgc gag gcc tcg gtc gtc gtg gtc tgt ctc cca cgc tcg ccc       672
Val Ile Arg Glu Ala Ser Val Val Val Val Cys Leu Pro Arg Ser Pro
    210                 215                 220 gag aca ttc aac ctc ata tcg gac gct gag ttc gac cag atg aga cag       720
Glu Thr Phe Asn Leu Ile Ser Asp Ala Glu Phe Asp Gln Met Arg Gln
225                 230                 235                 240 tgc ggc ctg ctg atc aac gtg tcg cgc ggc ggc atc gtg gac gag aag       768
Cys Gly Leu Leu Ile Asn Val Ser Arg Gly Gly Ile Val Asp Glu Lys
                245                 250                 255 gcc ctc gtc gct gcg ctg agg gag ggc aag atc gcc ggc gcc ggc aca       816
Ala Leu Val Ala Ala Leu Arg Glu Gly Lys Ile Ala Gly Ala Gly Thr
            260                 265                 270 gat gta tac tcc cag gaa ccg gcc gag ccg aat aac aac gtc ctg ctc       864
Asp Val Tyr Ser Gln Glu Pro Ala Glu Pro Asn Asn Asn Val Leu Leu
        275                 280                 285
```

```
gcc gcg gac acg gcg gac ctc aat ctc gtc acg acg ccg cat ctg gcc      912
Ala Ala Asp Thr Ala Asp Leu Asn Leu Val Thr Thr Pro His Leu Ala
290                 295                 300 tgg tac gcg gag gag acg ttt gat aac tac agc cga gcc tgc agg gcg      960
Trp Tyr Ala Glu Glu Thr Phe Asp Asn Tyr Ser Arg Ala Cys Arg Ala
305                 310                 315                 320 aac gtc gcc ggc ttc gtc acg aca tcg gaa ccc aag tat agg gtt cac     1008
Asn Val Ala Gly Phe Val Thr Thr Ser Glu Pro Lys Tyr Arg Val His
            325                 330                 335 taa                                                                  1011

<210> SEQ ID NO 2
<211> LENGTH: 336
<212> TYPE: PRT
<213> ORGANISM: Mycelia sterilia

<400> SEQUENCE: 2

Met Ala Gln Ala Gln Pro Gln Thr His Trp Val Ile Val Ala Leu Glu
 1               5                  10                  15

Thr Phe Phe Cys Pro Leu Pro Asp Phe Thr Leu Pro Ala Pro His Thr
            20                  25                  30

Cys Glu Phe Arg Asn Tyr Asp Arg Thr Arg Pro Asp Gln Ile Ala Glu
        35                  40                  45

Arg Ile Arg Asp Ala Asp Ile Val Ile Met Thr Ile Leu Pro Met Pro
50                  55                  60

Ala Asp Val Leu Ser Ala Glu Ala Ser Pro Arg Leu Lys Met Leu Ser
65                  70                  75                  80

Ile Ile Ala Ser Gly Thr Asp Thr Val Asp Leu Ala Thr Cys Arg Ala
                85                  90                  95

Arg Gly Ile Val Val Ala Asn Thr Pro His Cys Asn Val Thr Thr Val
            100                 105                 110

Thr Glu His Val Phe Ala Leu Tyr Phe Ala Thr Arg Arg Ser Ile Val
        115                 120                 125

Ala Thr His Leu Leu Thr Arg Ala Gly Asp Trp Val Thr Lys Gly Ser
130                 135                 140

Gln Gln Ser Thr Met Asn Gly Pro Asp Gly Lys Pro Pro Met Thr Cys
145                 150                 155                 160

Arg Asp Glu Leu Val Gly Ile Ile Gly Tyr Gly Ala Ile Gly Lys Asn
                165                 170                 175

Val Glu Thr Met Ala Arg Ser Leu Gly Met Lys Thr Val Ile Ala Gly
            180                 185                 190

His Lys Gly Ala Ala Ser Thr Pro Glu Gly Arg Ala Pro Phe Glu Thr
        195                 200                 205

Val Ile Arg Glu Ala Ser Val Val Val Cys Leu Pro Arg Ser Pro
210                 215                 220

Glu Thr Phe Asn Leu Ile Ser Asp Ala Glu Phe Asp Gln Met Arg Gln
225                 230                 235                 240

Cys Gly Leu Leu Ile Asn Val Ser Arg Gly Gly Ile Val Asp Glu Lys
                245                 250                 255

Ala Leu Val Ala Ala Leu Arg Glu Gly Lys Ile Ala Gly Ala Gly Thr
            260                 265                 270

Asp Val Tyr Ser Gln Glu Pro Ala Glu Pro Asn Asn Asn Val Leu Leu
        275                 280                 285

Ala Ala Asp Thr Ala Asp Leu Asn Leu Val Thr Thr Pro His Leu Ala
290                 295                 300
```

```
Trp Tyr Ala Glu Glu Thr Phe Asp Asn Tyr Ser Arg Ala Cys Arg Ala
305                 310                 315                 320

Asn Val Ala Gly Phe Val Thr Thr Ser Glu Pro Lys Tyr Arg Val His
                325                 330                 335
```

<210> SEQ ID NO 3
<211> LENGTH: 13
<212> TYPE: PRT
<213> ORGANISM: Mycelia sterilia

<400> SEQUENCE: 3

```
Ala Asn Val Ala Gly Phe Val Thr Thr Ser Glu Pro Lys
1               5                   10
```

<210> SEQ ID NO 4
<211> LENGTH: 7
<212> TYPE: PRT
<213> ORGANISM: Mycelia sterilia

<400> SEQUENCE: 4

```
Ala Gly Asp Trp Val Thr Lys
1               5
```

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer 1
<220> FEATURE:
<221> NAME/KEY: base
<222> LOCATION: (3)
<223> OTHER INFORMATION: n = a, g, c, or t
<220> FEATURE:
<221> NAME/KEY: base
<222> LOCATION: (6)
<223> OTHER INFORMATION: n = a, g, c, or t
<220> FEATURE:
<221> NAME/KEY: base
<222> LOCATION: (9)
<223> OTHER INFORMATION: r = a or g
<220> FEATURE:
<221> NAME/KEY: base
<222> LOCATION: (12)
<223> OTHER INFORMATION: n = a, g, c, or t
<220> FEATURE:
<221> NAME/KEY: base
<222> LOCATION: (15)
<223> OTHER INFORMATION: n = a, g, c, or t
<220> FEATURE:
<221> NAME/KEY: base
<222> LOCATION: (18)
<223> OTHER INFORMATION: n = a, g, c, or t

<400> SEQUENCE: 5
gtngtnacra anccngcnac                                            20

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence:Primer 2
<220> FEATURE:
<221> NAME/KEY: base
<222> LOCATION: (3)
<223> OTHER INFORMATION: n = a, g, c, or t
<220> FEATURE:
<221> NAME/KEY: base
<222> LOCATION: (6)
<223> OTHER INFORMATION: n = a, g, c, or t

```
<220> FEATURE:
<221> NAME/KEY: base
<222> LOCATION: (9)
<223> OTHER INFORMATION: y = t or c
<220> FEATURE:
<221> NAME/KEY: base
<222> LOCATION: (15)
<223> OTHER INFORMATION: n = a, g, c, or t

<400> SEQUENCE: 6
gcnggngayt gggtnac                                              17

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:Primer 3

<400> SEQUENCE: 7
aagggatccc agcagagcac gatgaa                                    26

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence:Primer 4

<400> SEQUENCE: 8
gcaggctcgg ctgtagttat caaa                                      24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Primer 5

<400> SEQUENCE: 9
taatacgact cactataggg                                           20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Primer 6

<400> SEQUENCE: 10
aattaaccct cactaaaggg                                           20

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence:Primer 7

<400> SEQUENCE: 11
aagcttgtaa ggagatatac atggcccaag cacaacca                       38

<210> SEQ ID NO 12
<211> LENGTH: 29
<212> TYPE: DNA
<213> ORGANISM: Artificial Sequence
<220> FEATURE:
```

-continued

```
<223> OTHER INFORMATION: Description of Artificial Sequence:Primer 8

<400> SEQUENCE: 12
atgcaagctt tagtgaaccc tatacttgg                                    29
```

(R)-2-HYDROXY-3-PHENYLPROPIONATE (D-PHENYLLACTATE) DEHYDROGENASE AND GENE ENCODING THE SAME

BACKGROUND OF THE INVENTION

1. Field of the Invention

The present invention relates to a novel D-phenyllactic acid dehydrogenase (occasionally abbreviated to "D-PLDH" hereinafter) for producing optically active 2-hydroxy acid derivatives, such as (R)-2-hydroxy-3-phenylpropionic acid (occasionally abbreviated to "D-phenyllactic acid" hereinafter) or derivatives thereof, and to a gene encoding this enzyme.

2. Background Art

D-phenyllactic acid is a precursor of the substance PF1022 [cyclo(D-lactyl-L-N-methylleucyl-D-3-phenyllactyl-L-N-methylleucyl-D-lactyl-L-N-methylleucyl-D-3-phenyllactyl-L-N-methylleucyl)] which is produced by the filamentous fungus strain PF1022 (*Mycelia sterilia*, FERM BP-2671) that belongs to Agonomycetales (Sasaki, T. et al., J. Antibiotics, 45, 692 (1992)). Recently, an enzyme which directly produces the substance PF1022 and a gene of this enzyme were revealed (WO01/18179A1). Further, it is known that when a phenyllactic acid derivative is added from outside during the culture of the substance PF1022-producing strain in a liquid medium, a novel substance PF1022 can be produced into which the added phenyllactic acid derivate is incorporated (WO 97/20945). In this case, a precursor to be added is desirably an (R)-2-hydroxy derivative.

Certain kinds of enzymes produced by microorganisms are known to specifically produce optically active compounds, such as D-lactic acid (Taguchi, H. et al., J. Biol. Chem., 266, 12588 (1991)). Further, there have been a number of reports on methods of producing industrially useful compounds such as (R)-2-hydroxy-4-phenylbutyric acid by using certain kinds of enzymes or microorganisms which produce useful enzymes (Japanese Patent No. 2750017, Japanese Patent No. 2752754, Japanese Patent No. 2774341, Japanese Patent No. 2873236, Japanese Patent Publication No. 61271/1994, Japanese Patent Laid-open Publication No. 197774/1994, and Japanese Patent Laid-open Publication No. 75797/1998). Enzymzatic reactions are characterized in producing a target compound more selectively and efficiently than chemical syntheses. On the other hand, it is necessary to search enzymes that specifically act on target compounds because substrate specificity of each enzyme is strict. So far, there has been no report on a dehydrogenase enzyme which is specific to D-phenyllactic acid derived from microorganisms.

SUMMARY OF THE INVENTION

The present inventors have succeeded in isolating an enzyme which specifically reduce phenylpyruvic acid and produce D-phenyllactic acid, namely D-phenyllactic acid dehydrogenase (D-PLDH), and a gene encoding this enzyme. Further, the inventors have succeeded in abundantly expressing this gene in *Escherichia coli*.

An object of the present invention is to provide a D-phenyllactic acid dehydrogenase.

Another objective of the present invention is to provide a gene which encodes the D-phenyllactic acid dehydrogenase.

Still another objective of the present invention is to provide a recombinant vector and a transformant for expressing the D-phenyllactic acid dehydrogenase, and a method of producing the D-phenyllactic acid dehydrogenase.

Another objective of the present invention is to provide a mass production system of the substance PF1022 and derivatives thereof and a method of producing the same.

A D-phenyllactic acid dehydrogenase according to the present invention is a protein comprising an amino acid sequence selected from the group consisting of the following sequences:

(a) the amino acid sequence of SEQ ID NO: 2, and (b) a modified amino acid sequence of the amino acid sequence of SEQ ID NO: 2 that has one or more modifications selected from a substitution, a deletion, an addition and an insertion and has D-phenyllactic acid dehydrogenase activity.

A D-phenyllactic acid dehydrogenase gene according to the present invention comprises a nucleotide sequence encoding the D-phenyllactic acid dehydrogenase.

Further, a D-phenyllactic acid dehydrogenase gene according to the present invention comprises a nucleotide sequence selected from the group consisting of the following sequences:

(c) the DNA sequence of SEQ ID NO: 1, (d) a nucleotide sequence that has at least 70% homology with the DNA sequence of SEQ ID NO: 1 and encodes a protein having D-phenyllactic acid dehydrogenase activity, (e) a modified DNA sequence of the DNA sequence of SEQ ID NO: 1 that has one or more modifications selected from a substitution, a deletion, an addition and an insertion and encodes a protein having D-phenyllactic acid dehydrogenase activity, and (f) a nucleotide sequence that hybridizes with the DNA sequence of SEQ ID NO: 1 under stringent conditions and encodes a protein having D-phenyllactic acid dehydrogenase activity.

A recombinant vector according to the present invention comprises a D-phenyllactic acid dehydrogenase gene according to the present invention.

A transformant according to the present invention is a host comprising a recombinant vector according to the present invention.

A process of producing a D-phenyllactic acid dehydrogenase according to the present invention comprises steps of culturing a transformant according to the present invention and collecting the D-phenyllactic acid dehydrogenase from the culture medium.

A system for producing the substance PF1022 according to the present invention is a substance PF1022-producing microorganism transformed with a recombinant vector according to the present invention.

A process of producing the substance PF1022 according to the present invention comprises steps of culturing a substance PF1022-producing microorganism transformed with a recombinant vector according to the present invention and collecting the substance from the culture medium.

DETAILED DESCRIPTION OF THE INVENTION

Deposition of Microorganisms

Figure 1:
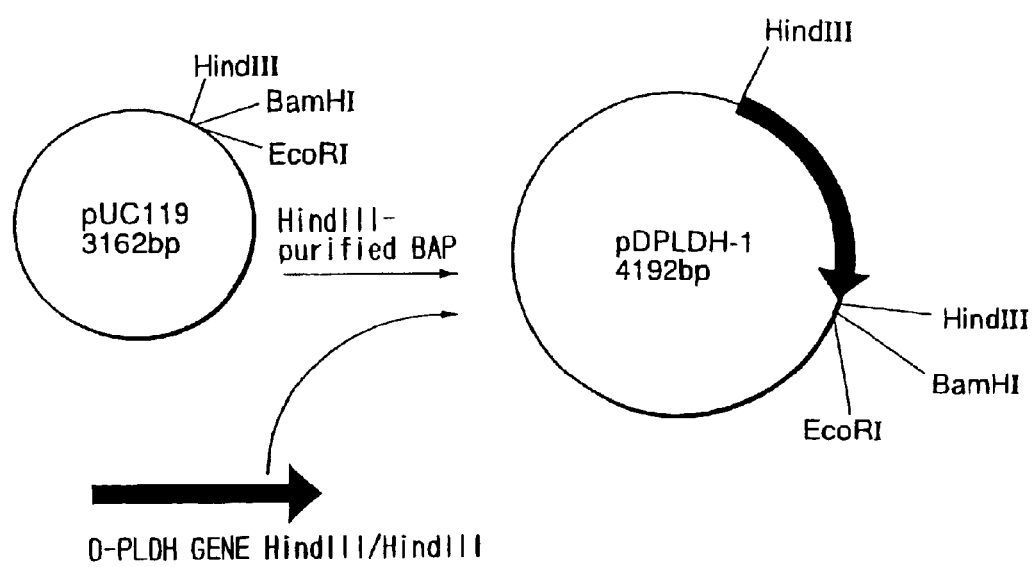
FIG. 1 shows a method of constructing plasmid pDPLDH-1.

The strain PF1022 described in Example 1-1 was deposited with the International Patent Organism Depositary, National Institute of Advanced Industrial Science and Technology (Tsukuba Central 6, 1-1 Higashi 1-Chome, Tsukuba, Ibaraki, Japan), dated Jan. 24, 1989. The accession number is FERM BP-2671.

The *Escherichia coli* (DH5α) strain transformed with plasmid pDPLDH-1 described in Example 3-3 was deposited with the International Patent Organism Depositary, National Institute of Advanced Industrial Science and Technology, dated Apr. 12, 2000. The accession number is FERM BP-7545.

Gene and Protein

According to the present invention, there are provided a D-phenyllactic acid dehydrogenase and a gene thereof.

An enzyme according to the present invention acts on 2-oxo-3-phenylpropionic acid (occasionally referred to as "phenylpyruvic acid" hereinafter) and reduces it to convert to (R)-2-hydroxy-3-phenylpropionic acid. Derivatives or analogues of D-phenyllactic acid can be prepared by previously modifying the substrate, phenylpyruvic acid.

Examples of derivatives of D-phenyllactic acid include p-aminophenyllactic acid, p-nitrophenyllactic acid, and p-hydroxyphenyllactic acid. In this case, for example, p-aminophenylpyruvic acid, p-nitrophenylpyruvic acid, and p-hydroxyphenylpyruvic acid can be used as a substrate for synthesizing the D-phenyllactic acid derivatives.

Examples of analogues of D-phenyllactic acid include (R)-2-hydroxy-4-phenylbutyric acid which is used as a material for an anti-hypertension agent. In this case, for example, 2-oxo-4-phenylbutyric acid can be used as a substrate for synthesizing the D-phenyllactic acid analogue.

In sequence (b), the number of modifications can be, for example, one to several, more specifically 1 to 6.

In sequence (e), the number of modifications can be, for example, one to dozens.

In sequence (b) and sequence (e), multiple modifications, which can be the same or different, can be introduced.

Sequence (d) can have preferably at least 80%, more preferably at least 90%, and most preferably at least 95% homology to the DNA sequence of SEQ ID NO: 1.

In sequence (f), the term "stringent conditions" means that a membrane after hybridization is washed at a high temperature in a solution of low salt concentration, for example, at a 0.2×SSC concentration (1×SSC: 15 mM trisodium citrate, 150 mM sodium chloride) in a 0.1% SDS solution at 60° C. for 15 minutes.

For sequence (b), whether it "has D-phenyllactic acid dehydrogenase activity" or not can be evaluated, for example, by providing a substrate for the D-phenyllactic acid dehydrogenase (e.g., phenylpyruvic acid) and a reduction-type coenzyme, i.e., nicotinamide adenine dinucleotide phosphate (NADPH), reacting a protein to be tested, and then measuring physicochemical changes generated by the enzyme reaction, such as a change in optical density of nicotinamide adenine dinucleotide phosphate and/or a quantitative change in the product, i.e., D-phenyllactic acid (see Example 3).

For sequences (d), (e) and (f), whether they "encode a protein having D-phenyllactic acid dehydrogenase activity" or not can be evaluated, for example, by expressing a nucleotide sequence to be tested in a host, reacting the resulting protein with a substrate for the D-phenyllactic acid dehydrogenase (e.g., phenylpyruvic acid) and a reduction-type coenzyme, i.e., nicotinamide adenine dinucleotide phosphate (NADPH), and then measuring physicochemical changes generated by the enzyme reaction, such as a change in optical density of nicotinamide adenine dinucleotide phosphate and/or a quantitative change in the product, i.e., D-phenyllactic acid (see Example 3).

Given the amino acid sequence of an enzyme according to the present invention, nucleotide sequences encoding it can be easily determined, and various nucleotide sequences encoding the amino acid sequence depicted in SEQ ID NO: 2 can be selected. Thus, nucleotide sequences encoding an enzyme according to the present invention include any DNA sequence encoding the same amino acid sequence and having degenerative codons, in addition to a part or all of the DNA sequence of SEQ ID NO: 1, and further include RNA sequences corresponding to those sequences.

The origin of an enzyme and a gene according to the present invention is not particularly restricted and any microorganism that can produce an enzyme according to the present invention can be used; the substance PF1022-producing microorganism (*Mycelia sterilia*, FERM BP-2671) is preferable.

The N-terminal amino acid sequence of an enzyme according to the present invention can be determined, for example, by applying the enzyme onto SDS-polyacrylamide electrophores is, electrically transferring the resulting enzyme band to a polyvinyliden fluoride (PVDF) membrane or the like, and then analyzing it by a protein sequencer.

The internal amino acid sequence of an enzyme according to the present invention can be determined, for example, by partially digesting the enzyme with a proteinase or the like and then carrying out the abovementioned steps after the SDS-polyacrylamide gel electrophoresis and an isolation step using reversed phase chromatography.

A gene according to the present invention can be obtained, for example, as follows.

A genomic DNA is extracted from a substance PF1022-producing microorganism and cleaved with appropriate restriction enzymes, after which a library comprising the genomic DNA of the substance PF1022-producing microorganism is constructed using a phage vector. Alternatively, the total RNA is extracted from the substance PF1022-producing microorganism, cDNA corresponding to mRNA is prepared by a reverse transcriptase reaction using an oligo dT as a primer, after which a library comprising the cDNA of the substance PF1022-producing microorganism is constructed using a phage vector.

Appropriate primers are synthesized based on the N-terminal amino acid sequence and the internal amino acid sequence of D-PLDH. The polymerase chain reaction (PCR) is carried out using these primers and the genomic DNA or cDNA derived from the substance PF1022-producing microorganism as a template, and thus the DNA fragment of the D-PLDH gene is amplified. The genomic library or the cDNA library is screened using this DNA fragment as a probe. In this way, the whole region of the D-phenyllactic acid dehydrogenase gene or a region necessary for the expression can be isolated. After determining the base sequences of these DNA fragments, appropriate restriction enzyme cleavage sites are introduced upstream of the translation start codon and downstream of the translation stop codon by PCR or the like to obtain a gene fragment which contains the D-phenyllactic acid dehydrogenase gene exclusively.

Recombinant Vector

According to the present invention, there is provided a recombinant vector comprising a nucleotide sequence encoding a D-phenyllactic acid dehydrogenase.

The procedure and method for constructing a recombinant vector according to the present invention can be any of those commonly used in the field of genetic engineering.

Examples of the vector as used herein include vectors which can be incorporated into a host chromosome DNA and vectors having a self-replicable autonomous replication sequence which can be present as a plasmid in a host cell, for example, pUC vectors (e.g., pUC18 and pUC118), pBluescript vectors (e.g., pBluescript II KS+), and plasmids such as pBR322. One or more copies of the gene can be present in a host cell.

A recombinant vector according to the present invention can be constructed, for example, by operably ligating a promoter and a terminator, upstream and downstream of the nucleotide sequence encoding a D-phenyllactic acid dehydrogenase, respectively, and, if appropriate, operably ligating a gene marker and/or other regulatory sequences.

The ligation of a promoter and a terminator to a gene according to the present invention and the insertion of an expression unit into a vector can be carried out by known methods.

A promoter and a terminator to be used in the present invention are not particularly limited. Examples include regulatory sequences of genes of glycolysis enzymes, such as 3-phosphoglycerate kinase and glutaraldehyde-3-phosphate dehydrogenase; regulatory sequences of genes of amino acid-synthesizing enzymes, such as tryptophan synthase; regulatory sequences of genes of hydrolytic enzymes, such as amylase, protease, lipase, and cellulase; regulatory sequences of genes of oxidation-reduction enzymes, such as nitrate reductase, orotidine-5'-phosphate dehydrogenase, and alcohol dehydrogenase; and regulatory sequences of genes derived from a substance PF1022-producing microorganism, such as Abp1 described in WO01/18219A1, which is highly expressed in the substance PF1022-producing microorganism.

A protein of the present invention can be expressed as a fusion protein by ligating a gene according to the present invention to a foreign gene encoding a translation region of another protein.

The introduction of a gene marker can be carried out, for example, by introducing an appropriate restriction enzyme cleaving site into a regulatory sequence by the PCR method, inserting this into a plasmid vector, and ligating a selective marker gene such as a drug resistance gene and/or a gene complementing a nutritional requirement A selective marker can be appropriately selected depending on the technique for selecting a transformant. For example, a drug resistance gene or a gene complementing a nutritional requirement can be used. Examples of the drug resistance gene include genes conferring resistance to destomycin, benomyl, oligomycin, hygromycin, G418, pleomycin, phosphinothricin, ampicillin, kanamycin, or the like. Examples of the gene complementing a nutritional requirement include arqB, pyr4, trpC, TRP1, niaD, LEU2, and URA3.

Production of Transformant and D-phenyllactic Acid Dehydrogenase

According to the present invention, there is provided a host transformed with the abovementioned vector.

A host to be used in the present invention is not particularly restricted, and any microorganism which can be used as a host for genetic recombination can be used. Examples of the host to be used include microorganisms, namely certain bacteria or fungi, preferably *Escherichia coli*, lactobacillus, actinomycetes, yeasts, and filamentous fungi, more preferably filamentous fungi which produce the substance PF1022, and most preferably the strain PF1022 (*Mycelia sterilia*, FERM BP-2671) and variants thereof.

A recombinant vector for the gene expression can be introduced into a host by an ordinary method. Examples of the method for the introduction include electroporation methods, polyethylene glycol methods, aglobacterium methods, lithium methods, and calcium chloride methods. A method suitable to each host cell can be selected. The polyethylene glycol method is preferable when a substance PF1022-producing microorganism is used as a host.

A transformant can be cultured according to an ordinary method by using a medium, culture conditions and the like which are appropriately selected. As a medium, conventional components can be used for a medium. As a carbonsource, glucose, sucrose, starch syrup, dextrin, starch, glycerol, molasses, animal and vegetable oils, and the like can be used. As a nitrogen source, organic or inorganic nitrogen compounds, such as soybean powder, wheat germ, pharma media, cornsteep liquor, cottonseed lees, bouillon, polypeptone, malt extract, yeast extract, ammonium sulfate, sodium nitrate, and urea, can be used. If necessary, sodium, potassium, calcium, magnesium, cobalt, chlorine, phosphoric acid, sulfuric acid, and other inorganic salts which can produce ions, such as potassium chloride, calcium carbonate, dipotassium hydrogenphosphate, manganese sulfate, and copper sulfate, can be effectively added. If necessary, various vitamins such as thiamine (e.g., thiamine hydrochloride), amino acids such as glutamic acid (e.g., sodium glutamate) and asparagine (e.g., DL-asparagine), nucleic acid components such as nucleotides, and selective drugs such as antibiotics can be added. Further, organic and inorganic substances can be appropriately added to promote microbial growth and enhance production of an enzyme of the present invention.

The cultivation can be carried out by a shaking culture method under an aerobic condition, an agitation culture method with aeration, or an aerobic submerged culture method. In particular, an aerobic submerged culture method is most preferable. Some hosts can be cultured by an anaerobic culture method.

A pH range of the medium is, for example, about 6 to 8. The cultivation can be carried out by a shaking culture method under an aerobic condition, or an agitation culture method with aeration. An appropriate culture temperature is 15° C. to 60° C., preferably about 20° C. to 40° C. Cultivation time is, for example, 60 to 240 hours, preferably about 8 to 168 hours.

The cultivation is terminated when the amount of the D-phenyllactic acid dehydrogenase in the medium reaches its peak, and the D-phenyllactic acid dehydrogenase is isolated and purified from the culture.

An enzyme according to the present invention can be isolated and purified from the culture by crushing the cultured microbial cells and treating the resulting cell-free extract using an ordinary purification means. For example, microbial cells recovered by centrifuging or filtering the culture are crushed by physical means, for example, by ultrasonic treatment, using sea sands, or a mortar and pestle, or ground using a ball mill, a French press, a freezing crusher, a blender, a mixer or the like, after which debris are removed by centrifugation to obtain a cell-free extract. In case where the cells recovered from the culture by centrifugation or filtration are not immediately crushed, they can be stored by freezing or lyophilization and crushed when needed. Then, an enzyme having the activity can be obtained by treating the cell-free extract using an ordinary purification method, such as an ammonium sulfate fractionation method, an ion-exchange chromatography method, an affinity chromatography method, an adsorption chromatography method, and a gel filtration method, singly or in combination.

According to the present invention, there is provided a mass-production system of a D-phenyllactic acid dehydrogenase. Examples of a host to be used as a system for mass-production of the D-phenyllactic acid dehydrogenase include *Escherichia coli*, lactobacillus, actinomycetes, yeasts, and filamentous fungi.

An enzyme according to the present invention transforms phenylpyruvic acid into D-phenyllactic acid. On the other hand, the substance PF1022 is synthesized from four molecules of L-leucine, two molecules of D-lactic acid and two molecules of D-phenyllactic acid by a cyclic depsipeptide-synthesizing enzyme. Accordingly, D-phenyllactic acid corresponds to a raw material for synthesizing the substance PF1022. Therefore, the substance PF1022 can be produced in large quantities if D-phenyllactic acid is abundantly expressed in a substance PF1022-producing microorganism. Accordingly, the present invention provides a mass production system of the substance PF1022, characterized in that the system is transformed so as to express an enzyme according to the present invention. The substance PF1022 is useful as a vermifuge for animals (Sasaki, T. et al., J. Antibiotics, 45, 692 (1992)).

A substance PF1022-producing microorganism usable as a system for mass-production of substance PF1022 is preferably a substance PF1022-producing filamentous fungus, most preferably the substance PF1022-producing strain *Mycelia sterilia* (FERM BP-2671).

A PF1022-producing microorganism can be further transformed by a gene other than an enzyme gene according to the present invention. For example, the production of substance PF1022 can be improved by introducing a gene of an enzyme which acts in the scheme for synthesizing the substance PF1022, occasionally along with a powerful promoter. An example of such a gene is a cyclic depsipeptide-synthesizing enzyme (WO01/18179A1).

In a host which does not synthesize a substrate on which an enzyme according to the present invention acts, i.e., phenylpyruvic acid, derivative or homologous substance thereof, D-phenyllactic acid, derivative or homologous substance thereof can be produced by adding the deficient substrate, derivative or homologous substance of the substrate to the culture or by transforming the host with a gene encoding the deficient substrate, derivative or homologous substance of the substrate. An example of such an enzyme gene is a gene involved in a biosynthesis pathway from chorismic acid to p-aminophenylpyruvic acid (WO01/23542A1).

In a host in which the gene involved in the biosynthesis pathway from chorismic acid to p-aminophenylpyruvic acid, p-aminophenylpyruvic acid is synthesized, and an enzyme according to the present invention converts the p-aminophenylpyruvic acid to p-aminophenyllactic acid. As a result, the converted p-aminophenyllactic acid makes a raw material for the substance PF1022 production, so that a substrate PF1022 derivative of which a benzene ring is modified with an amino group at the para position, i.e., [cyclo(D-lactyl-L-N-methylleucyl-D-3-(4-aminophenyl)lactyl-L-N-methylleucyl-D-lactyl-L-N-methylleucyl-D-3-phenyllactyl-L-N-methylleucyl)], is synthesized. A substance PF1022 derivative modified with a functional group such as an amino group is useful as a raw material for synthesizing a highly active substance PF1022 derivative.

A recombinant vector used for transformation is preferably an expression vector in which a regulatory sequence (e.g., promoter and terminator), which functions in the substance PF1022-producing microorganism, is operably ligated to an enzyme gene according to the present invention, or most preferably an expression vector in which a regulatory sequence, which functions in the strain PF1022 (*Mycelia sterilia*, FERM BP-2671), is operably ligated to an enzyme gene according to the present invention. An example of a powerful promoter to enhance the expression is Abp1 promoter (WO01/18219A1).

EXAMPLE

The present invention is further illustrated by the following examples that are not intended as a limitation of the invention.

Example 1

Isolation and Purification of D-PLDH

1. Preparation of Microbial Cells

The substance PF1022-producing microorganism (*Mycelia sterilia*, FERM BP-2671) was subjected to UV radiation or NTG treatment to induce mutation, and the resulting substance PF1022-producing strain 432-26, in which PF1022 productivity was improved, was inoculated into 50 ml of a seed medium [1% yeast extract, 1% malt extract, 2% polypeptone, 2.5% glucose, 0.1% dipotassium hydrogenphosphate, 0.05% magnesium sulfate (pH 7.0)] (WO 01/18179A1) in an appropriate container and cultured at 26° C. for 3 days with shaking to prepare a primary seed culture. This culture was inoculated into 500 ml of medium described in WO97/20945 in an appropriate container and incubated at 26° C. for 3 days using a rotary shaker to prepare a secondary seed culture. This culture was inoculated into 500 ml of the same medium in an appropriate container and incubated at 26° C. for 4 to 6 days using a rotary shaker. After cultivation, the resulting culture was filtered with suctioning using commercial nylon cloth and a Buchner funnel and at the same time, microbial cells were washed with deionized water. A cake of the microbial cells thus obtained was immediately frozen at −80° C. and dried in a freeze-dryer for 2 nights. The freeze-dried cells thus prepared could be stored at −80° C. in an airtight container.

2. Extraction and Purification of D-PLDH

An admixture of 2 μl of 0.1 M phenylpyruvic acid, 2 μl of 0.1 M NADPH, buffer solution A (10 mM Tris-HCl, 10 mM DTT, pH 8) and an optional volume of an enzyme sample solution to make a total volume of 100 μl was reacted at 26° C. for 2 hours. After terminating the reaction by heat treatment, the reaction solution was analyzed using HPLC (column: L-column ODS 4.6 Ø×150 mm (Chemicals Evaluation and Research Institute, Japan ), mobile phase: 0.1 M sodium sulfate: acetonitrile (3.9:1) isocratic, flow rate: 1 ml/min, temperature: 40° C., UV detection: 210 nm) and the amount of phenyllactic acid produced was defined as the activity of this enzyme. Further, optical activity of the enzyme reaction product was analyzed using another HPLC (column: CHIRALPAK WH 0.46 Ø×25 cm (Daicel Chemical Industries, Ltd. ), mobile phase: aqueous 25 mM copper sulfate solution, flow rate: 1 ml/min, temperature: 40° C., UV detection: 210 nm).

The following steps were all carried out at 4° C. Approximately 70 g of freeze-dried cells obtained in Example 1-1 were ground overnight in a ball mil (pot external diameter: 210 Ø mm, ball diameter: 35 Ø mm, Tokyo Garasu Kikai Co., Ltd. ). The resulting fine cell powder was thoroughly suspended in 1.5 L of an extraction buffer solution (50 mM Tris-HCl, 10 mM DTT, 50 mM potassium chloride, pH 8) added to the cells. The cell suspension was gently stirred for about 1 hour using a magnetic stirrer. Next, the cell suspension was centrifuged at 8000 rpm for 30 minutes to recover about 1.2 L of supernatant using a high-speed refrigerated centrifuge SCR20B (rotor No. RPR9, Hitachi Koki Co., Ltd.). The recovered supernatant was applied onto a column (26 Ø×300 mm) filled with Red Sepharose CL6B (Amersham Pharmacia) as a vehicle. The column was washed with buffer solution A until an unadsorbed fraction completely disappeared, after which a protein eluted with buffer solution A containing 1 M potassium chloride was fractionated. A pooled active fraction was subjected to gel chromatography using a column (26 Ø×950 mm) filled with Superdex 200 (Amersham Pharmacia) as a vehicle. The active fraction was immediately applied onto MonoQ10/10 (Amersham Pharmacia). After washing the column with buffer solution A, adsorbed proteins were eluted using 0–0.3 M potassium chloride gradient. The resulting pooled active fraction was diluted 10 times with buffer solution A and applied onto a column (16 Ø×100 mm) filled with AMP agarose (Amersham Pharmacia). An unadsorbed fraction was recovered and immediately applied onto a column (5 Ø×50 mm) filled with hydroxyapatite. An unadsorbed fraction was recovered and adsorbed again onto MonoQ10/10. Proteins were eluted using 0–0.2 M potassium chloride gradient. Polyacrylamide electrophoresis showed that the active fraction contained an almost single protein having a molecular weight of about 38 kDa.

3. Determination of Internal Part Amino Acid Sequence of D-PLDH

The protein obtained in Example 1-2 was concentrated and isolated using SDS-polyacrylamide gel electrophoresis and electrically transferred onto a PVDF membrane. The protein transferred onto the PVDF membrane was stained with Coomassie Brilliant Blue to confirm its presence and location. A piece of the PVDF membrane where the protein was present was cut out and subjected to the analysis of the N-terminal amino acid sequence using a protein sequencer, which, however, resulted in failure.

The protein obtained in Example 1-2 was concentrated and isolated using SDS-polyacrylamide gel electrophoresis and the gel was stained with Coomassie Brilliant Blue. A piece of gel containing the protein of interest was cut out. This gel was repeatedly washed with 200 µl of a decoloring solution (0.2 M ammonium bicarbonate, 50% acetonitrile, pH 8.0) in a small test tube to wash out Coomassie Brilliant Blue from the gel, after which the gel was dried under reduced pressure. To the half-dried gel was added 5 µl of buffer solution B (0.2 M ammonium bicarbonate, 0.02% Tween 20, pH 8.0) and then a 1/100 molar volume of trypsin was added. The admixture was allowed to stand for about 10 minutes to disperse the enzyme in the gel, after which 200 µl of buffer solution B was added and the protein was digested with the enzyme at 37° C. for 48 hours. The enzyme reaction was terminated with trifluoracetic acid and the reaction solution was recovered. The gel was thoroughly washed with 200 µl of a washing solution (0.1% trifluoracetic acid, 60% acetonitrile) and the wash was mixed with the previously recovered reaction solution. Washing was further repeated twice to recover the trypsin digest. The recovered trypsin digest was dried under reduced pressure, after which 60 µl of distilled water was added to make a peptide fragment sample digested by trypsin. This sample was subjected to chromatography for fractionation (column: C18, 0.21 Ø×220 mm, gradient: 0.1% trifluoracetic acid, 5% acetonitrile –0.085% trifluoracetic acid, 35% acetonitrile) using a Model 172µ preparative HPLC system (Perkin-Elmer Applied Biosystem). Of the peptide fragment peaks obtained, two peptide fragments were analyzed for amino acid sequences and the following sequences were determined.

Peptide fragment 1: ANVAGFVTTSEPK (SEQ ID NO: 3)
Peptide fragment 2: AGDWVTK (SEQ ID NO: 4)

Example 2

Isolation of cDNA of D-PLDH

1. Isolation of cDNA and Construction of cDNA Library

The substance PF1022-producing microorganism (*Mycelia sterilia*, FERM BP-2671) was subjected to UV radiation or NTG treatment to induce mutation, and the resulting substance PF1022-producing strain 432-26, in which PF1022 productivity was improved, was inoculated into 10 ml of a seed medium [1% yeast extract, 1% malt extract, 2% polypeptone, 2.5% glucose, 0.1% dipotassium hydrogenphosphate, 0.05% magnesium sulfate (pH 7.0)] (WO01/18179A1) in a test tube and incubated at 26° C. for 3 days with shaking. The seed culture was inoculated into 50 ml of the medium described in WO97/20945 in an appropriate container and incubated at 26° C. for 6 days using a rotary shaker, after which the cells were recovered by centrifugation. The cells thus obtained were frozen with liquid nitrogen and then smashed with a mortar and pestle. The whole RNA was isolated from the smashed cells using ISOGEN (Nippon Gene) according to the attached protocol. Further, mRNA was purified from the whole RNA using a mRNA Purification Kit (Amersham Pharmacia) according to the attached protocol.

cDNA was synthesized from the mRNA thus obtained using a Time Saver cDNA Synthesis Kit (Amersham Pharmacia) according to the attached protocol. This cDNA was inserted into a phage vector, Lambda ZAP II (Stratagene Co.). The recombinant phage vector thus constructed was subjected to in vitro packaging using a Gigapack III Gold Packaging Extract (Stratagene Co.) according to the attached protocol. Thereafter, *Escherichia coli* XL1-Blue MRF' strain was infected with this recombinant phage and cultured on a plate to form plaques. The cDNA library thus constructed had a plaque forming unit of $6.8 \times 10^5$. Further, this cDNA library was amplified according to the protocol attached to the Lambda ZAP II. *Escherichia coli* XL1-Blue MRF' strain was infected with the recombinant phage in this amplified cDNA library and cultured on a plate to form plaques.

2. Isolation of Partial DNA Fragment of D-PLDH Gene

The following two primers were synthesized based on the sequences of peptide fragments 1 and 2 obtained in Example 1-3.

Primer 1: 5'-GTIGTIACRAAICCNGCNAC-3' (SEQ ID NO: 5)

Primer 2: 5'-GCIGGIGAYTGGGTNAC-3'  (SEQ ID NO: 6)

Using these primers, PCR was carried out using the genomic DNA isolated from the substance PF1022-producing microorganism (FERM BP-2671) as a template, by the method described in WO01/18179A1. The PCR was conducted in 100 µl of reaction solution using 80 ng of the genomic DNA as a template and adding 2.5 units of ExTaq DNA polymerase (Takara Shuzo Co., Ltd.), the attached buffer solution and dNTP mixture, and the two kinds of primers each at a final concentration of 0.5 µM, under the following conditions: at 94° C. for 5 minutes, [at 94° C. for one minute, at 58° C. for one minute, at 72° C. for 30 seconds]×40 cycles, and at 72° C. for 7 minutes; storage at 4° C. Analysis of the reaction solution by 2% agarose gel electrophoresis showed that a DNA fragment of about 550 bp was amplified. This DNA fragment was recovered from the agarose gel using a commercial Sephaglas BandPrep Kit (Amersham Pharmacia). The recovered DNA fragment and pT7Blue T-Vector (Novagen, Inc.) were ligated using a DNA Ligation Kit ver. 2 (Takara Shuzo Co., Ltd.) according to the attached protocol.

The base sequence of the DNA fragment thus cloned was determined using a DNA Sequencing Kit dRhodamine Terminator Cycle Sequencing Ready Reaction (Perkin-Elmer) and an ABI PRISM 310 Genetic Analyzer (Perkin-Elmer) according to the attached protocol. As a result, the base sequence of the isolated DNA fragment was revealed to be homologous to that of D-α-keto acid specific dehydrogenase gene and was strongly suggested to be a part of the D-PLDH gene of interest.

3. Cloning of the Whole Region of cDNA of D-PLDH

The following two primers were newly synthesized based on the sequences of the DNA fragments obtained in Example 2-2.

```
Primer 3:
5'-AAGGGATCCCAGCAGAGCACGATGAA-3'    (SEQ ID NO: 7)

Primer 4:
5'-GCAGGCTCGGCTGTAGTTATCAAA-3'     (SEQ ID NO: 8)
```

A PCR product, which was amplified by PCR with the primer 3 and primer 4 using the DNA fragment obtained in Example 2-2 as a template, was used as a probe in screening the cDNA library. The PCR was conducted in 100 µl of reaction solution using 500 ng of the pT8Blue plasmid vector, into which the DNA fragment obtained in Example 2-2 was inserted, as a template, and adding 2.5 units of ExTaq DNA polymerase (Takara Shuzo Co., Ltd.), the attached buffer solution and dNTP mixture, and the two kinds of the primers each at a final concentration of 0.5 µM, under the following conditions: at 94° C. for 5 minutes, [at 94° C. for one minute, at 60° C. for one minute, at 72° C. for 30 seconds]×40 cycles, and at 72° C. for 7 minutes; storage at 4° C. The resulting reaction solution was subjected to 2% agarose gel electrophoresis, which confirmed the presence of a DNA fragment of about 530 bp. This DNA fragment was recovered from the agarose gel using a Sephaglas BandPrep Kit (Amersham Pharmacia). The recovered DNA fragment was labeled using an ECL Direct DNA/RNA Labeling Detecting System (Amersham Pharmacia) according to the attached protocol, and used as a nucleic acid probe for hybridization.

A blotting membrane Hibond N+ (Amersham Pharmacia) was placed on the plate prepared in Example 2-1, on which plaques were formed, to copy the plaques. This membrane was treated according to the method of Makabe (Kazuhiro Makabe, Visual Experimental Note Series, Biotechnology Experiments Illustrated 4, in Cell Technology Supp., 125–133, 1997, published by Shujunsha) to immobilize the DNA on the membrane. In this treatment, the membrane was washed with 5×SSC. Using an ECL Direct DNA/RNA Labeling Detecting System (Amersham Pharmacia), the labeled nucleic acid probe and the phage DNA immobilized on the membrane were hybridized according to the attached protocol and then the plaques in which the labeled nucleic acid was hybridized were detected In this way, a positive phage containing a 5' upstream region and a 3' downstream region homologous to the probe was selected.

The positive phage was treated according to the protocol attached to a Lambda ZAP II (Stratagene Co.) to prepare a plasmid into which the cDNA gene of D-PLDH was inserted.

4. Determination of Base Sequence

Sequencing was carried out using the plasmid, into which the cDNA gene of D-PLDH thus isolated was inserted, as a template and primer 5: 5'-TAATACGACTCACTATAGGG-3' (SEQ ID NO: 9) and/or primer 6: 5'-AATTAACCCTCACTAAAGGG-3' (SEQ ID NO: 10) as primers The sequencing was carried out using a DNA Sequencing Kit dRhodamine Terminator Cycle Sequencing Ready Reaction (Perkin-Elmer) and an ABI PRISM 310 Genetic Analyzer (Perkin-Elmer) according to the attached protocol. From the results obtained, regions where the base sequence was not known were further subjected to sequencing using primers newly designed based on already-sequenced base sequences. In this way, the base sequence of the 1509-bp cDNA gene of D-PLDH inserted into the plasmid was determined.

The analysis of this sequence revealed that a 1011-bp open reading frame (ORF) was present. The protein extrapolated from this ORF had 336 amino acid residues and a molecular weight of 36.5 kDa, and was homologous to D-lactic acid dehydrogenase or the like. The highest homology was shown with glycerate dehydrogenase and the homology was 37%. The base sequence and the amino acid sequence of the ORF of the D-PLDH gene of the present invention thus isolated are shown in SEQ ID NO: 1 and SEQ ID NO: 2 in the sequencing list, respectively.

Example 3

Mass Production of D-PLDH by Mass Expression of D-PLDH Gene

1. Preparation of D-PLDH Gene for Gene Expression

PCR was carried out using the plasmid prepared in Example 2-3 as a template, primer 7: 5'-AAGCTTGTAAGGAGATATACATGGCCCAAGCAC AACCA-3' (SEQ ID NO: 11) to which were added a HindIII site at the 5'-end, a stop codon just behind, and further a ribosome binding site just behind, and primer 8: 5'-ATGCAAGCTTTAGTGAACCCTATACTTGG-3' (SEQ ID NO: 12) to which only a HindIII site was added at the 5'-end, in order to amplify the D-PLDH gene in which HindIII sites were introduced to both ends. The PCR was carried out in 20 µl of reaction solution using 80 ng of the plasmid DNA as a template, one unit of TaKaRa LA-Taq DNA polymerase (Takara Shuzo Co., Ltd.), the attached buffer solution and dNTP mixture, 25 mM magnesium chloride, and 100 µM primers, under the following conditions: at 94° C. for one minute, (at 98° C. for 15 seconds, at 68° C. for 3 minutes)×30 cycles, and at 72° C. for 10 minutes. The resulting reaction solution was subjected to 1% agarose gel electrophoresis to confirm the presence of an about 1000-bp DNA fragment, which was recovered from the agarose gel using a Sephaglas Band Prep Kit (Amersham Pharmacia). The recovered PCR product and pT7B Blue T-Vector (Novagen, Inc.) were ligated using a DNA Ligation Kit ver. 2 (Takara Shuzo Co., Ltd.) according to the attached protocol. A plasmid ligated with D-PLDH was introduced into *Escherichia coli* DH 5α and amplified and the plasmid DNA was recovered using Concert Rapid Plasmid Purification Systems (Gibco BRL Products).

The gene sequence of D-PLDH thus amplified was confirmed using the primer derived from the D-PLDH gene used in Example 2-4 and a primer derived from the base sequence of pT7 plasmid vector. Sequencing was carried out using a DNA Sequencing Kit BigDye Terminator Cycle Sequencing Ready Reaction (Perkin-Elmer) and an ABI PRISM 310 Genetic Analyzer (Perkin-Elmer) according to the attached protocol.

After confirming the sequence, 24 µl of a DNA solution containing pT7 plasmid vector to which about 12 µg of the D-PLDH gene was ligated, 3 µl of HindIII (Toyobo Co., Ltd.), and 3 µl of the attached buffer solution were thoroughly mixed and the mixture was reacted at 37° C. for 18 hours. Next, the reaction solution was subjected to 1% agarose gel electrophoresis to confirm an about 1000-bp DNA fragment. This fragment was recovered from the agarose gel using a Sephaglas Band Prep Kit (Amersham Pharmacia) to obtain the D-PLDH gene for expression.

2. Construction of Gene Expression Vector

A solution containing about 2.5 µg of commercial pUC119 (Takara Shuzo Co., Ltd.) was reacted with HindIII (Toyobo Co., Ltd.) and the attached buffer solution at 37° C. for 18 hours, after which DNA was recovered by phenol extraction. To this DNA were added 3 µl of alkaline phosphatase C75 (Takara Shuzo Co., Ltd.), 3 µl of the attached buffer solution, and 24 µl of sterile water and then the admixture was reacted at 50° C. for 30 minutes to remove the terminal phosphoric acid. The dephosphorylated DNA was recovered by phenol extraction and dissolved in 3 µl of TE buffer solution (10 mM Tris-HCl, 1 mM EDTA, pH 8). Plasmid pDPLDH-1 was constructed by ligating 5 µl of the D-PLDH gene for expression prepared in Example 3-1 and 0.5 µl of pUC119 vector which was digested with HindIII and dephosphorylated at the termini, using a DNA Ligation Kit ver. 2 (Takara Shuzo Co., Ltd.) according to the attached protocol (FIG. 1).

3. Expression of D-PLDH in *Escherichia coli*

Cells of *Escherichia coli* DH 5α (Toyobo Co., Ltd.), into which pDPLDH-1 was introduced, were spread on an LB agar medium containing 50 µg/ml ampicillin. After culturing statically at 37° C. for 18 hours, grown *E. coli* DH 5α cells were inoculated into 2 ml of LB medium containing 50 µg/ml ampicillin and cultured at 37° C. for 18 hours with shaking to prepare a seed culture. A portion of the seed culture was inoculated into 2 ml each of the same medium in 10 test tubes. Shake culture was started at 37° C., after 5 hours IPTG was added to a final concentration of 1 mM, and shake culture was further continued for 2 hours. After culturing, cells were recovered by centrifugation, washed with buffer solution A described in Example 1-2, and then suspended in 2.5 ml of buffer solution A. The resulting suspension was treated in an ultrasonicator under an ice-cold condition, cell debris was removed by centrifugation, and the supernatant, a crude enzyme solution, was thus obtained. *Escherichia coli* DH 5α which was transformed using pUC119 without the D-PLDH gene was used as a control.

A 150 µl portion of buffer solution A containing 250 µM NADPH and 250 µM phenylpyruvic acid was dispensed into wells of a 96-well microtiter plate, 50 µl each of the crude enzyme solution was added and mixed immediately using a pipette, and a change in absorption at 340 nm at 26° C. was measured. The measurement was carried out using an Absorption Microassay Reader BioLumin 960 (Molecular Dynamics) to trace a decrease in absorption with time after the start of the reaction. The amount of the enzyme which oxidized 1 µmol of NADPH per minute was set to be one unit. Results are shown in Table 1 as the enzyme activity of the crude enzyme solution.

TABLE 1

Dehydrogenase activity in crude enzyme solution

| Strain from which crude enzyme solution was prepared | Enzyme activity |
|---|---|
| pUC119-carrying strain | $7.30 \times 10^{-3}$ |
| pDPLDH-1-carrying strain | $1.01 \times 10^{-1}$ |

The values shown were converted into [unit/ml of crude enzyme solution].

Thus, the *Escherichia coli* DH5α transformed with pDPLDH-1 showed D-PLDH activity about 13 times higher than the *E. coli* DH5α transformed with pUC119. Results of analysis using an optical dividing column confirmed that the product of the strain carrying the D-PLDH gene was D-phenyllactic acid. The gene according to the present invention was confirmed to be the D-PLDH gene.

Further, the obtained crude enzyme solution was processed using Mono Q10/10 under the conditions described in Example 1-2 to prepare a partially purified enzyme solution. This partially purified enzyme solution was applied onto a 96-well microtiter with different concentrations of the substrate, phenylpyruvic acid, to measure enzyme activity. Further, enzyme activity was also measured with an alternative substrate, pyruvic acid, in place of phenylpyruvic acid. Results of measurement are shown in Table 2, in which the reaction rate with pyruvic acid was set to be 100.

TABLE 2

Relative enzyme activity with different reaction substrates

| Reaction substrate | Relative reaction rate (rate with phenylypyruvic acid = 100) |
|---|---|
| Phenylpyruvic acid | 100 |
| Pyruvic acid | 10 |

Thus, it was revealed that the enzyme according to the present invention was evidently different in its characteristics from known lactic acid dehydrogenases and the like (Japanese Patent No. 2750017; Taguchi, H. et al., J. Biol. Chem., 266, p.12588 (1991)) and was a novel enzyme in terms of both amino acid sequence and enzymatic characteristics.

What is claimed is:

1. An isolated polynucleotide which encodes a protein having an amino acid sequence of SEQ ID NO: 2.

2. The isolated polynucleotide according to claim 1, which comprises the DNA sequence of SEQ ID NO: 1.

3. A isolated polynucleotide sequence selected from the group consisting of the following sequences:

(a) the DNA sequence of SEQ ID NO: 1, (b) a nucleotide sequence that has at least 95% homology with the DNA sequence of SEQ ID NO: 1 and encodes a protein having D-phenyllactic acid dehydrogenase activity, (c) a nucleotide sequence that hybridizes with the DNA sequence of SEQ ID NO: 1 under stringent conditions and encodes a protein having D-phenyllactic acid dehydrogenase activity wherein the stringent conditions comprise a wash at a 0.2×SSC concentration (1×SSC: 15 mM trisodium citrate, 150 mM sodium chloride) in a 0.1% SDS solution at 60° C. for 15 minutes.

4. A recombinant vector comprising the polynucleotide of any one of claims 1 to 3.

5. A host cell transformed with the recombinant vector of claim 4.

6. The host cell according to claim 5, which expresses a D-phenyllactic acid dehydrogenase.

7. The host cell according to claim 5, which is a microorganism which produces cyclo(D-lactyl-L-N-methylleucyl-D-3-phenyllactyl-L-N-methylleucyl-D-lactyl-L-N-methylleucyl-D-3-phenyllactyl-L-N-methylleucyl) (PF1022).

8. A process of producing a D-phenyllactic acid dehydrogenase, comprising the steps of culturing the host cell of claim 5, and collecting the D-phenyllactic acid dehydrogenase from the culture medium.

9. The host cell according to claim 6, which is a microorganism which produces cyclo(D-lactyl-L-N-methylleucyl-D-3-phenyllactyl-L-N-methylleucyl-D-lactyl-L-N-methylleucyl-D-3-phenyllactyl-L-N-methylleucyl) (PF1022).

10. A process of producing a D-phenyllactic acid dehydrogenase, comprising the steps of culturing the host cell of claim 6, and collecting the D-phenyllactic acid dehydrogenase from the culture medium.

11. A process of producing a D-phenyllactic acid dehydrogenase, comprising the steps of culturing the host cell of claim 7, and collecting the D-phenyllactic acid dehydrogenase from the culture medium.

12. A process of producing a D-phenyllactic acid dehydrogenase, comprising the steps of culturing the host cell of claim 9, and collecting the D-phenyllactic acid dehydrogenase from the culture medium.

* * * * *